US012788333B2

(12) United States Patent
Maule et al.

(10) Patent No.: US 12,788,333 B2
(45) Date of Patent: Nov. 10, 2026

(54) COMPUTED TOMOGRAPHY (CT) IMAGING SYSTEM GANTRY MOTION DETECTION

(71) Applicant: GE Precision Healthcare LLC, Waukesha, WI (US)

(72) Inventors: Joseph Daniel Maule, Waukesha, WI (US); Eric Christopher Aasen, Pewaukee, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 338 days.

(21) Appl. No.: 18/674,988

(22) Filed: May 27, 2024

(65) Prior Publication Data

US 2025/0359829 A1 Nov. 27, 2025

(51) Int. Cl.
*A61B 6/03* (2006.01)
*A61B 6/00* (2006.01)

(52) U.S. Cl.
CPC ............ *A61B 6/032* (2013.01); *A61B 6/4447* (2013.01); *A61B 6/527* (2013.01)

(58) Field of Classification Search
None
See application file for complete search history.

(56) References Cited

U.S. PATENT DOCUMENTS 6,890,100 B2 5/2005 Reznicek et al.
2003/0159508 A1 8/2003 Halsmer
2004/0037436 A1* 2/2004 Rui ........................ H04R 3/005 381/92
2013/0221964 A1* 8/2013 Shafiee Haji Abadi ..................... A61B 5/055 324/322

FOREIGN PATENT DOCUMENTS

EP 2664360 A2 * 11/2013 ........... A61N 5/1048
WO WO-2014184574 A1 * 11/2014 ............... G21K 1/10

* cited by examiner

*Primary Examiner* — Suman K Nath
(74) *Attorney, Agent, or Firm* — Daugherty & Del Zoppo, III Co. LPA

(57) ABSTRACT

A computed tomography imaging system includes a gantry and a rotating frame rotatably supported in the gantry and carrying at least one component for producing, transmitting or receiving X-ray radiation, a first motion sensor configured to sense a first motion of the gantry in a first plane and generate a first signal indicative of the first motion and that has a first noise floor, a second motion sensor configured to concurrently sense the first motion of the gantry in the first plane and generate a second signal indicative of the first motion and that has a second noise floor, and motion signal processing circuitry configured to combine the first signal and the second signal to generate a first combined signal indicative of the first motion, wherein the first combined signal has a third noise floor that is lower than the first noise floor and the second noise floor.

20 Claims, 12 Drawing Sheets

COMPUTED TOMOGRAPHY (CT) IMAGING SYSTEM GANTRY MOTION DETECTION

FIELD

The following generally relates to computed tomography (CT), and more particularly to detecting a motion of a gantry of a computed tomography (CT) imaging system.

BACKGROUND

A computed tomography (CT) scanner includes a gantry and a rotating frame rotatably supported by a bearing in the gantry. The rotating frame is configured to rotate around an examination region along an axis of rotation about a center of rotation (i.e., an isocenter). The rotating frame carries components such as at least an X-ray source, an X-ray radiation sensitive detector array, a high voltage generator, an X-ray radiation collimator, a gantry cooling system, etc. For axial and/or helical scanning, the rotating frame rotates around the examination region, the X-ray source emits X-ray radiation that traverses the isocenter (and a subject and/or object in the examination region), and is detected by the X-ray radiation sensitive detector array.

The X-ray radiation sensitive detector array generates projection data (line integrals) indicative of the sensed X-ray radiation. A reconstructor reconstructs the projection data and generates volumetric image data. Voxels of the reconstructed volumetric image data are displayed as a two-dimensional (2-D) CT image and/or a three-dimensional (3-D) CT image using gray scale values corresponding to a relative radiodensity. The gray scale values reflect the attenuation characteristics of the scanned subject and/or object and generally show structure such as anatomical structures within the scanned subject and/or physical structure within the scanned object.

In image space, the isocenter has been utilized as a center of a reconstructed CT image. As such, motion of the isocenter during scanning can manifest as artifact, e.g., blur, etc., in the reconstructed CT image, reducing image quality and/or diagnostic quality of the CT image. This may result in additional X-ray radiation dose exposure to the patient, e.g., where the patient is rescanned due to poorer image quality, and X-ray radiation is ionizing radiation, which can damage and/or kill cells. Sources of such motion include an imbalance of the masses carried by the rotating frame, inadequate mounting of the gantry to the examination room floor, etc.

The masses are initially balanced on the rotating frame during manufacturing, where components are installed on the rotating gantry at designated locations in accordance with assembly procedures, the rotating frame is rotated, motion is detected with motion detectors, and one or more balance weights are installed on one or more balance weight supports to balance the masses about the axis of rotation. During shipping, installation at a user site, replacement of a component on the rotating frame for preventive maintenance, replacement of a component on the rotating frame for corrective maintenance, use over time, etc., the masses may fall out of balance, creating an imbalance.

Procedures using motion sensors exist for confirming a rotating frame is balanced. Where the masses are no longer balanced, a rebalancing procedure can be performed to rebalance the masses. However, depending on the rotation speed of the rotating frame, a level of the motion signal may be small and fall within a noise floor of the motion sensor such that the motion signal cannot be distinguished from the noise and used for balancing purposes. Even when balanced, another source, such as the inadequate mounting of the gantry to the examination room floor, may result in a gantry motion signal that falls within a noise floor of the motion sensor such that it cannot be distinguished from the noise, even though the motion is large enough to negatively impact image quality.

In view of at least the foregoing, there is an unresolved need for an improved approach for detecting gantry motion of a CT imaging system.

SUMMARY

Aspects described herein address the above-referenced problems and others. This summary introduces concepts that are described in more detail in the detailed description. It should not be used to identify essential features of the claimed subject matter, nor to limit the scope of the claimed subject matter.

In one aspect, a computed tomography imaging system includes a gantry and a rotating frame. The rotating frame is rotatably supported in the gantry. The rotating frame carries at least one component for producing, transmitting or receiving X-ray radiation. The computed tomography imaging system further includes a first motion sensor configured to sense a first motion of the gantry in a first plane and generate a first signal indicative of the first motion. The first signal has a first noise floor. The computed tomography imaging system further includes a second motion sensor configured to concurrently sense the first motion of the gantry in the first plane and generate a second signal indicative of the first motion. The second signal has a second noise floor. The computed tomography imaging system further includes motion signal processing circuitry configured to combine the first signal and the second signal to generate a first combined signal indicative of the first motion. The first combined signal has a third noise floor that is lower than the first noise floor and the second noise floor.

In another aspect, a computer-implemented method includes detecting a first motion of a gantry of a computed tomography imaging system in a first plane with a first motion sensor. The computer-implemented method further includes generating a first signal indicative of the first motion. The first signal has a first noise floor. The computer-implemented method further includes detecting, concurrently with detecting the first motion with the first motion sensor, the first motion of the gantry with a second motion sensor. The computer-implemented method further includes generating a second signal indicative of the first motion. The second signal has a first noise floor. The computer-implemented method further includes combining the first signal and the second signal into a first combined signal. The first combined signal has a third noise floor that is lower than the first noise floor and the second noise floor.

In another aspect, a computer readable medium is encoded with computer executable instructions. The computer executable instructions, when executed by a processor, cause the processor to detect a first motion of a gantry of a computed tomography imaging system in a first plane with a first motion sensor. The computer executable instructions further cause the processor to generate a first signal indicative of the first motion. The first signal has a first noise floor. The computer executable instructions further cause the processor to detect, concurrently with detecting the first motion with the first motion sensor, the first motion of the gantry with a second motion sensor. The computer executable instructions further cause the processor to generate a second signal indicative of the first motion. The second signal has a first noise floor. The computer executable instructions further cause the processor to combine the first signal and the second signal into a first combined signal. The first combined signal has a third noise floor that is lower than the first noise floor and the second noise floor.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings in which like references indicate similar elements.

DETAILED DESCRIPTION

Embodiments of the present disclosure will now be described, by way of example, with reference to the figures, in which a system, a method and/or a computer readable medium includes instructions for detecting motion of a gantry of a computed tomography (CT) imaging system through a set of motion sensors using an approach that reduces a noise floor, allowing for detection of lower magnitude motion that would otherwise fall within the noise floor and not be distinguishable from the noise, absent the approach described herein. As described in greater detail below, in one instance the approach includes employing the motion sensors of the set of motion sensors to concurrently detect a same gantry motion and then combining the motion signals output by the motion sensors into a combined motion signal to reduce the noise floor.

Other processing includes integrating the combined motion signals, and reading out the integrated signal for further processing. In one instance, the sensed motion is utilized during manufacturing to balance masses carried by the rotating frame and/or at a user site to rebalance the masses during service after a component has been replaced. Additionally, or alternatively, the sensed motion is utilized to ensure the gantry is sufficiently mounted to the floor of an examination room. Additionally, or alternatively, the sensed motion is monitored over time to ensure the gantry motion stays within a predetermined allowable range.

Figure 1:
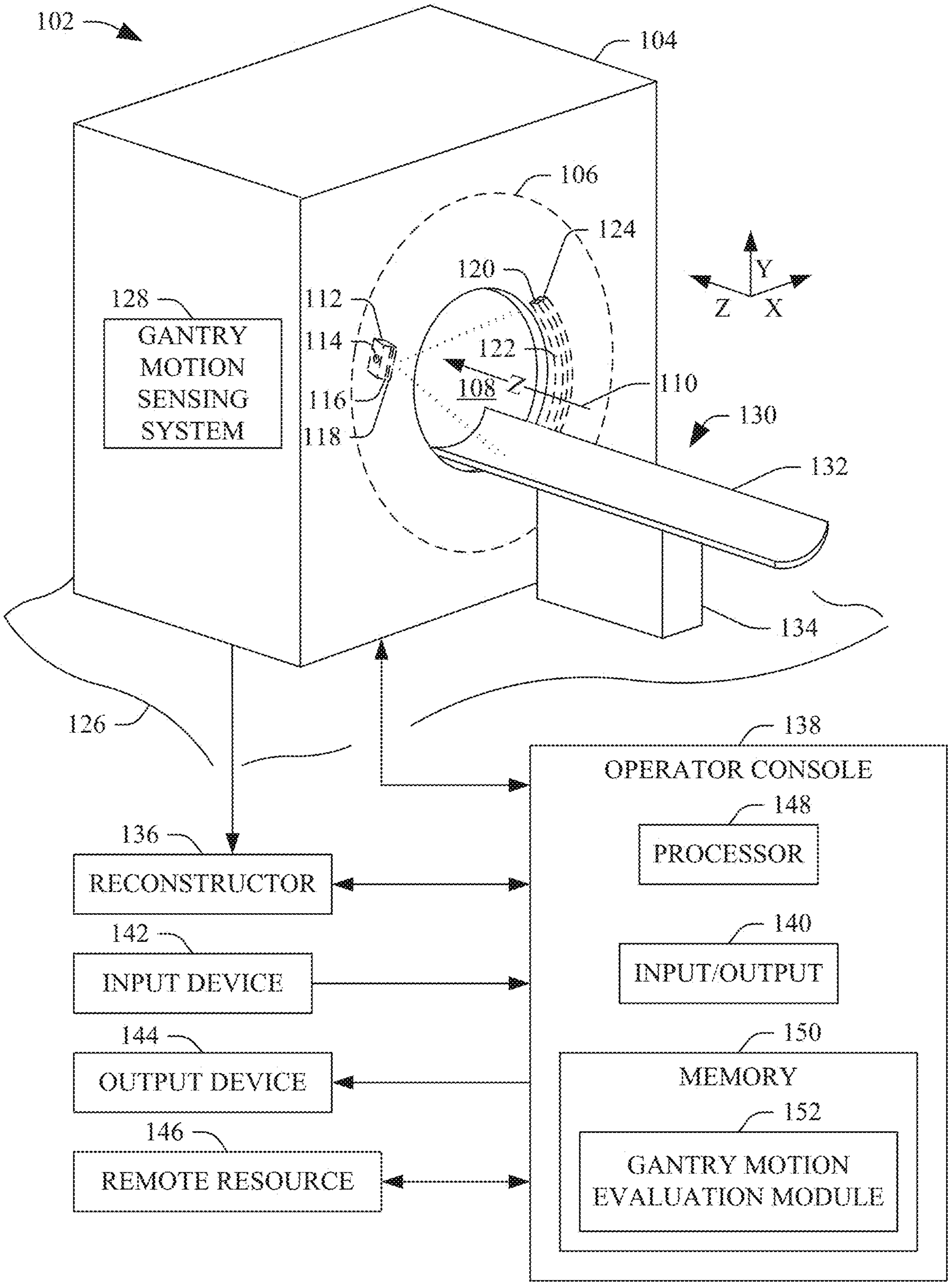
FIG. 1 schematically illustrates a non-limiting example of an imaging system configured for computed tomography imaging and including a gantry motion sensing system, in accordance with an embodiment(s) herein.

Initially referring to FIG. 1, a non-limiting example of an imaging system 102 such as a computed tomography (CT) imaging system is schematically illustrated. The imaging system 102 includes a gantry 104. In some instances, the gantry 104 is configured to tilt. The imaging system 102 further includes a rotating frame 106. The rotating frame 106 is rotatably supported in the gantry 104, e.g., via a bearing (e.g., a slip ring) or the like, and is configured to rotate around an examination region 108 about a rotational or z-axis 110, which extends through a center of rotation/a center of the examination region 108 (i.e., an isocenter). A gantry controller (not visible) is configured to control rotation of the rotating frame 106 and, if configured to tilt, tilting of the gantry 104.

An X-ray source assembly 112 is supported by the rotating frame 106 and rotates in coordination with the rotating frame 106. The X-ray source assembly 112 includes an X-ray source 114 such as an X-ray tube. The X-ray source 114 is configured to emit X-ray radiation having an energy in the X-ray diagnostic range (e.g., 20 keV to 150 keV). The X-ray assembly 112 may further include or is coupled to a filter 116 that characterizes an X-ray radiation dose profile and/or a collimator 118 that shapes the X-ray radiation to form a generally fan, wedge, cone, etc. shaped beam that traverses the examination region 108. An X-ray controller (not visible) is configured to control components of the X-ray assembly 112 such as X-ray radiation emission of the X-ray source 114, the collimator 118, etc.

An X-ray radiation sensitive detector array 120 includes a one-dimensional (1-D) or two-dimensional (2-D) array of rows of X-ray radiation sensitive detector elements 122 and is supported by the rotating frame 106 along an arc opposite the X-ray source 114, across the examination region 108. Each of the X-ray radiation sensitive detector elements 122 is in electrical communication with a data acquisition system (DAS) 124. The X-ray radiation sensitive detector elements 122 include an indirect conversion detector such as a scintillator/photodiode detector and/or a direct conversion detector such as a Cadmium Telluride (CdTe), a Cadmium Zinc Telluride (CZT), etc. detector. A DAS controller (not visible) controls the X-ray radiation sensitive detector array 120.

Figure 2:
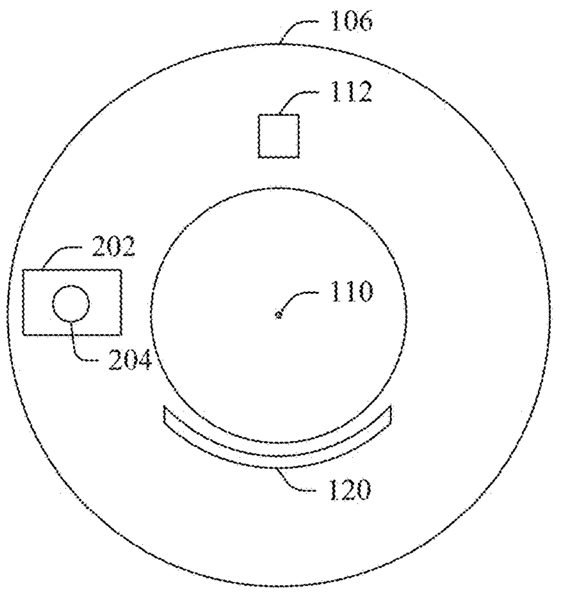
FIG. 2 schematically illustrates a non-limiting example of a rotating frame of the imaging system supporting components with different masses and balance weights, in accordance with an embodiment(s) herein.

Briefly turning to FIG. 2, a side view of the rotating frame 106 is schematically illustrated. In this example, the rotating frame 106 supports at least the X-ray source assembly 112, the X-ray radiation sensitive detector array 120, and at least one balance weight support 202, which is configured to carry one or more balance weights 204. In general, components utilized in the production, emission and/or detection of X-ray radiation have different shapes, sizes, masses, etc., and are installed on the rotating frame 106 at predetermined locations and within predetermined mechanical tolerances in accordance with an assembly procedure. The one or more balance weights 204 are installed on the at least one balance weight support 202 to evenly distribute the masses carried by the rotating frame 106 about the Z-axis 110.

Figure 3:
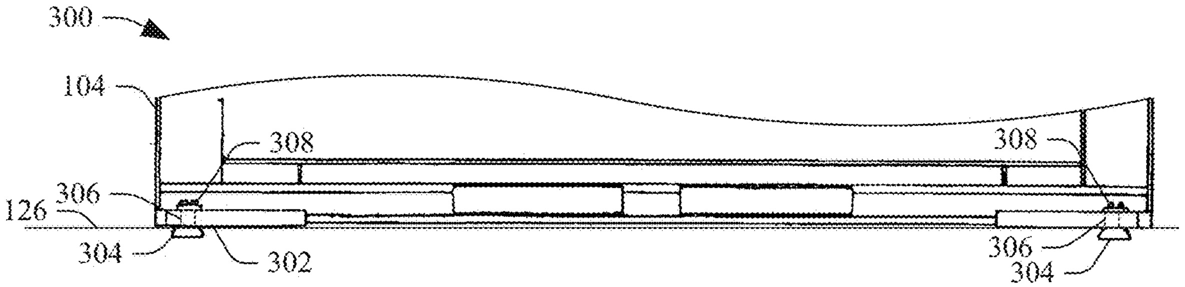
FIG. 3 schematically illustrates a non-limiting example of a portion of a gantry of the imaging system mounted to a support, in accordance with an embodiment(s) herein.

Returning to FIG. 1, the gantry 104 is mounted to a support 126. In this example, the support 126 is a floor of an examination room. Briefly turning to FIG. 3, an example of a bottom portion 300 of the gantry 104 mounted to the floor 126 is schematically illustrated. In this example, a mounting bracket 302 of the gantry 104 rests on a surface of the floor 126. Multiple mounting elements 304 are affixed to and/or integrated into the support 126. For each mounting element 304, a trunk 306 protrudes from the floor 126, through an opening in the mounting bracket 302, and into the mounting bracket 302. A securing mechanism 308 engages the trunk 306 and secures the mounting bracket 302, and, hence, the gantry 104, to the floor 126.

Returning to FIG. 1, the gantry 104 includes a gantry motion sensing system 128. The gantry motion sensing system 128 is configured to sense certain motions of the gantry 104, including gantry motion in a X-direction and motion in a Z-direction. In general, the gantry motion sensing system 128 employs multiple motion sensors of a set of motion sensors to concurrently detect a same gantry motion and then combines the motion signals generated by the multiple motion sensors, lowering the noise floor, allowing for detecting lower magnitude motion that would otherwise fall within the noise floor and not be readily detectable, absent the approach described herein.

In one instance, the sensed motion is utilized during manufacturing to balance masses carried by the rotating frame. In another instance, the sensed motion is utilized at a user site to rebalance the masses, e.g., during service after a component has been replaced. Additionally, or alternatively, the sensed motion is utilized to ensure the gantry is sufficiently mounted in an examination room floor. Additionally, or alternatively, the sensed motion is monitored over time to ensure the gantry motion stays within a predetermined allowable range. Additionally, or alternatively, the sensed motion is otherwise utilized.

Figure 4:
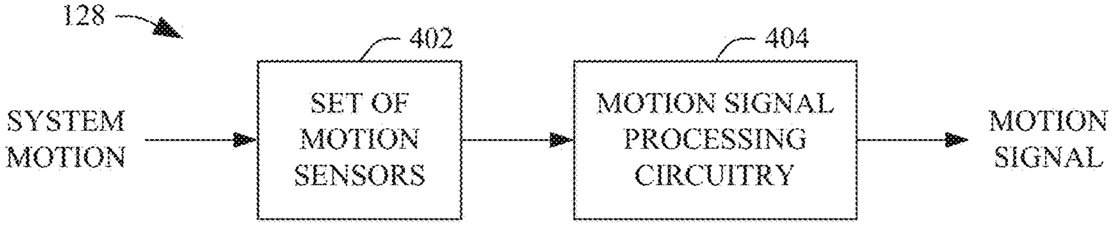
FIG. 4 schematically illustrates a non-limiting example of a block diagram of the gantry motion sensing system, in accordance with an embodiment(s) herein.

Briefly turning to FIG. 4, an example of a block diagram of the gantry motion sensing system 128 is schematically illustrated. The gantry motion sensing system 128 includes a set of motion sensors 402. In one instance, the set of motion sensors 402 includes a set of accelerometers configured to detect gantry motion in at least two axes/planes, e.g., along the X-direction and the Z-direction. The gantry motion sensing system 128 further includes motion signal processing circuitry 404. In one instance, the motion signal processing circuitry 404 is configured to combine the signals generated by the set of accelerometers to produce an acceleration signal indicative of gantry motion. Other processing includes integrating the combined signal to determine a velocity signal indicative of gantry motion. In one instance, the other processing further includes integrating the velocity signal to determine a displacement signal indicative of gantry motion. In another instance, the velocity signal is readout and further processed by other hardware and/or software to determine the displacement signal.

In one instance, the set of accelerometers includes at least two accelerometers configured to sense a gantry motion in a same plane (e.g., X or Z), and the motion signal processing circuitry 404 includes corresponding circuitry that averages the motion signals generated by the at least two accelerometers. In one instance, the averaging is based on a statistical analysis approach such as the square root of a sum of the squares/root-sum-square approach and/or the like. With respect to the noise, such an approach decreases a noise floor of the set of accelerometers relative to the individual accelerometers of the set of accelerometers, as shown in EQUATION 1:

EQUATION 1

$$\mathrm{Tot}Vnoise_{rms} = \frac{\sqrt{Vnoise_{1_{rms}}{}^2 + Vnoise_{2_{rms}}{}^2 + \ldots + Vnoise_{n_{rms}}{}^2}}{n},$$

where Total $Vnoise_{rms}$ represents a noise floor of a set of n accelerometers, $Vnoise_{rms}$ represents a noise floor of each of the individual n accelerometers, and n is equal to or greater than two. Where the noise for each of the n accelerometers is approximately a same noise level, i.e., $Vnoise_{1_{rms}} \approx Vnoise_{2_{rms}} \ldots \approx Vnoise_{n_{rms}}$, EQUATION 1 can be written as shown in EQUATION 2:

EQUATION 2

$$\text{Total } Vnoise_{rms} = \frac{\sqrt{n}}{n} Vnoise_{rms},$$

which indicates the noise floor of the set of n accelerometers decrease with the number of accelerometers by $$\frac{\sqrt{n}}{n}.$$

Figure 5:
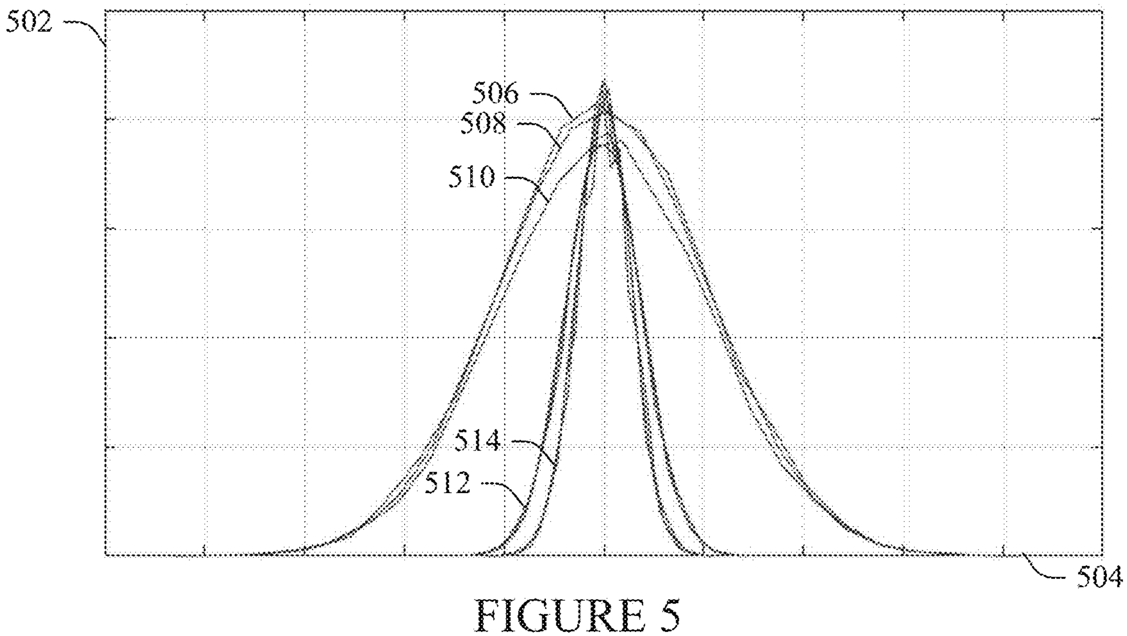
FIG. 5 graphically illustrates a total noise of a combination of sensors of the gantry motion sensing system as a function of a number of motion sensors, in accordance with an embodiment(s) herein.

Briefly turning to FIG. 5, a graphical representation showing a relationship between the noise floor of the set of n accelerometers and the number of accelerometers n is graphically illustrated. In FIG. 5, a first axis 502 represents signal magnitude, and a second axis 504 represents noise. A plot 506, a plot 508 and a plot 510 show the total noise for n=i, a plot 512 shows the total noise for n=j, and a plot 514 shows the total noise for n=k, where i, j and k are positive integers and i<j and j<k. From FIG. 5, as n increases from i to j to k, the noise floor of the set of n accelerometers decreases. In one non-limiting instance, examples of n include 2, 16, 30, more, less, or in between.

Returning to FIG. 1, a subject/object support 130 includes a tabletop 132 moveably coupled to a frame/base 134. In one instance, the tabletop 132 is slidably coupled to the frame/base 134 via a bearing or the like, and a drive system (not visible) including a controller, a motor, a lead screw, and a nut (or other drive system) translates the tabletop 132 along the frame/base 134 into and out of the examination region 108. The tabletop 132 is configured to support an object or subject in the examination region 108 for loading, scanning, and/or unloading the subject or object. A table controller (not visible) controls the drive system.

For a helical scan, the rotating frame 106 rotates in coordination with the tabletop 132 moving along the Z-axis 110, and active X-ray detector elements 122 of the X-ray radiation sensitive detector array 120 detect X-ray radiation over consecutive arc segments (integration periods) each revolution and generate respective signals. For an axial (step and shoot) scan, the tabletop 132 is positioned at a static position for each integration period and moves between integration periods. For each arc segment, the data acquisition electronics 124 processes each signal and generates projection data.

A reconstructor 136 reconstructs the projection data and generates volumetric (3-D) image data for a helical scan and/or individual axial (2-D) images for an axial step and shoot scan (which can be used in combination to generate volumetric image data). The volumetric image data and/or 2-D slices thereof, and/or the individual axial images can be visually presented, filmed, etc. Examples of suitable reconstruction algorithms include filtered back projection (FBP), advanced statistical iterative reconstruction (ASIR), conjugate gradient (CG), maximum likelihood expectation maximization (MLEM), model-based iterative reconstruction (MBIR), and/or other reconstruction algorithm.

A computing system 138 serves as an operator console of the system 102. The computing system 138 may include a computer, a workstation, etc. The computing system 138 includes input/output (I/O) 140. An input device 142 includes a keyboard, mouse, touchscreen, microphone, etc. The input device 142 is in electrical communication with the computing system 138 through the I/O 140 and/or otherwise. An output device 144 includes a human readable device such as a display monitor or the like. The output device 144 is in electrical communication with the computing system 138 through the I/O 140 and/or otherwise.

A remote resource 146 includes one or more of a server, a workstation, a Radiology Information System (RIS), a Hospital Information System (HIS), an electronic medical record (EMR), a Picture Archiving and Communications System (PACS), one or more other CT scanners, cloud processing resources (which includes shared remote data storage and/or computing power, including processing resources distributed over multiple locations/data centers), etc. The remote resource 146 is in electrical communication with the computing system 138 through the I/O 140 and/or otherwise.

The computing system 138 further includes at least one processor 148 such as a microprocessor (μP), a central processing unit (CPU), graphics processing unit (GPU), etc., and a computer readable medium 150 ("MEMORY"), which includes non-transitory medium and excludes transitory medium (signals, carrier waves, and the like). The computer readable medium/memory 150 at least includes a gantry motion evaluation module 152. As described in greater detail below, in one instance the gantry motion evaluation module 152 is configured to process motion signals from the gantry motion sensing system 128, e.g., in connection with balancing the masses carried by the rotating frame 106, ensuring adequate installation of the gantry 104 in an examination room, monitoring gantry motion over time, etc.

In one instance, this includes providing notices, messages, warnings, etc. regarding gantry motion. For example, in one instance the gantry motion evaluation module 152 provides a value of the motion in a plane along with a predetermined range of allowable motion in the plane. In another instance, the gantry motion evaluation module 152 invokes display of a pop up window or the like on a display monitor of the output device 144 with textual, graphical, etc. indicia indicating sensed motion with respect to the predetermined range. Additionally, or alternatively, the gantry motion evaluation module 152 invokes transmission of a text message, email, etc. to service personnel and/or the manufacturer in response to the sensed motion falling outside of the predetermined range. Other notices, messages, warnings, etc. are contemplated herein.

Figure 6:
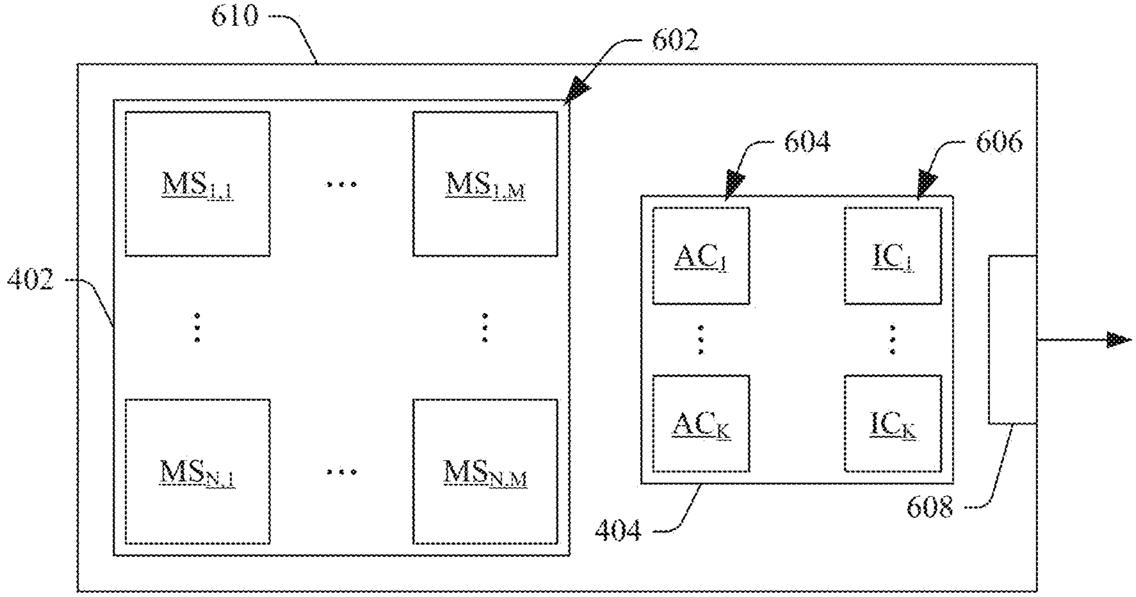
FIG. 6 schematically illustrates a non-limiting example of the gantry motion sensing system, in accordance with an embodiment(s) herein.

Turning now to FIG. 6, an example of the gantry motion sensing system 128 (FIG. 1) is schematically illustrated. The set of motion sensors 402 (FIG. 4) includes an N×M array of motion sensors 602, including a motion sensor $MS_{1,1}$, . . . , a motion sensor $MS_{N,1}$, . . . , a motion sensor $MS_{1,M}$, . . . and a motion sensor $MS_{N,M}$, where N is an integer equal to or greater than one, M is an integer equal to or greater than one, N is greater than one when M equals one, and M is greater than one when N equals one. In this example, each of the motion sensors in the N×M array of motion sensors 602 is a multi-axis motion sensor, where at least one axis is assigned to sense gantry motion in one axis/plane (e.g., the X-direction or the Z-direction), another axis is assigned to sense gantry motion in another axis/plane (e.g., the X-direction or the Z-direction), etc. In one instance, the motion sensors $MS_{1,1}$, . . . , $MS_{N,M}$ includes micro-electromechanical systems (MEMS) based multi-axis accelerometers packaged in an integrate chip (IC).

The motion signal processing circuitry 404 (FIG. 4) includes K averaging circuits 604, including an averaging circuit $AC_1$, . . . , and an averaging circuit $AC_K$, where K is an integer equal to the number of axes/planes being monitored. The averaging circuit $AC_1$ samples only the output acceleration values of each of the motion sensors of the N×M array of motion sensors 602 that correspond to the axis/plane assigned to the averaging circuit $AC_1$, . . . , and the processor $AC_K$ samples only the output acceleration values of each of the motion sensors of the N×M array of motion sensors 602 that correspond to the axis/plane assigned to the averaging circuit $AC_K$. The averaging circuit $AC_1$, . . . , and the averaging circuit $AC_K$ are configured to concurrently sample outputs of the N×M array of motion sensors 602. Each of the K averaging circuits 604 is configured to determine an average of the samples of the acceleration values corresponding motion sensors of the N×M array of motion sensors 602, e.g., based a square root of a sum of the squares/root-sum-square approach, and/or otherwise. In one instance, the averaging circuits $AC_1$, . . . , and $AC_K$ include MEMS based devices packaged in an IC.

The motion signal processing circuitry 404 further includes K integrating circuits 606, including an integrating circuit $IC_1$, . . . , and an integrating circuit $IC_K$. The integrating circuit $IC_1$ integrates the output of the averaging circuit $AC_1$, . . . , and the integrating circuit $IC_K$ integrates the output of the averaging circuit $AC_K$. In one instance, the integrating circuits $IC_1$, . . . , and $IC_K$ include MEMS based devices packaged in an IC.

The gantry motion sensing system 128 further includes readout electronics 608. The readout electronics 608 readout the signal integrated by the integrating circuit $IC_1$, . . . , and the signal integrated by the integrating circuit $IC_K$. In one instance, the readout electronics 608 are part of and/or in electrical communication with an electro-mechanical connector such as a socket of a plug and socket connector pair, e.g., a "female" socket including an outer housing and receptacle contacts. In this instance, a complementary electro-mechanical connector would include a plug of the plug and socket connector pair, e.g., a "male" plug including an outer housing and electrically conductive pins, etc.

In this example, the N×M array of motion sensors 602, the K averaging circuits 604, the K integrating circuits 606, and the readout electronics 608 are disposed on a common substrate 610 such as a circuit board, e.g., a printed circuit board (PCB), a printed wiring board (PWB), etc. In this example, the integrated signals are further processed off of the common substrate 610 to determine, e.g., displacement values for the motion in the axis/planes assigned to the averaging circuit $AC_1$, . . . , and the motion in the axis/planes assigned to the averaging circuit $AC_1$. In one instance, another hardware component and/or software in the gantry 104 determines the displacement values. Additionally, or alternatively, another hardware component and/or software outside of the gantry 104, e.g., in the operator console 138 determines the displacement values. For example, in one instance, the gantry motion evaluation module 152 is configured to determine the displacement values from the signals read off the common substrate 610.

Figure 7:
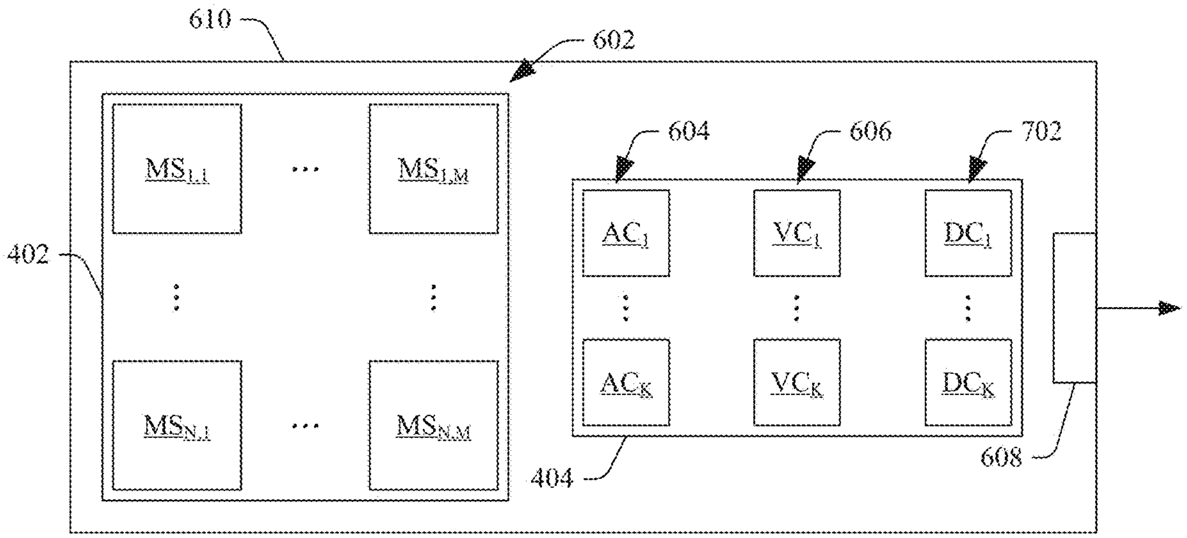
FIG. 7 schematically illustrates another non-limiting example of the gantry motion sensing system, in accordance with an embodiment(s) herein.

FIG. 7 schematically illustrates a variation of the gantry motion sensor system 128 (FIG. 1). In this example, the gantry motion sensing system 128 includes a second set of K integrating circuits 702, including an integrating circuit $IC_1$, . . . , and an integrating circuit $IC_K$. For explanatory purposes and clarity, the integrating circuit $IC_1$ of the set of K integrating circuits 606, . . . , and the integrating circuit $IC_K$ of the set of K integrating circuits 606 are referred to as the velocity circuit $VC_1$, . . . , and the velocity circuit $VC_K$, and the integrating circuit $IC_1$ of the second set of K integrating circuits 702, . . . , and the integrating circuit $IC_K$ of the second set of K integrating circuits 702 are referred to as the displacement circuit $DC_1$, . . . , and the displacement circuit $DC_K$.

The displacement circuit $DC_1$ of the second set of K integrating circuits 702 integrates the output of the velocity circuit $IC_1$ of the set of K integrating circuits 606 producing a displacement value for the motion in the axis/plane assigned to the averaging circuit $AC_1$, . . . , and the displacement circuit $IC_K$ of the second set of K integrating circuits 702 integrates the output of the velocity circuit $IC_1$ of the set of K integrating circuits 606 producing a displacement value for the motion in the axis/plane assigned to the averaging circuit $AC_K$. The readout electronics 608 readout the displacement values output by the displacement circuit $IC_1$, . . . , and the integrating circuit $IC_K$ of the second set of K integrating circuits 702. In another instance, the velocity computation and the displacement computation are performed in the in the same IC.

Figure 8:
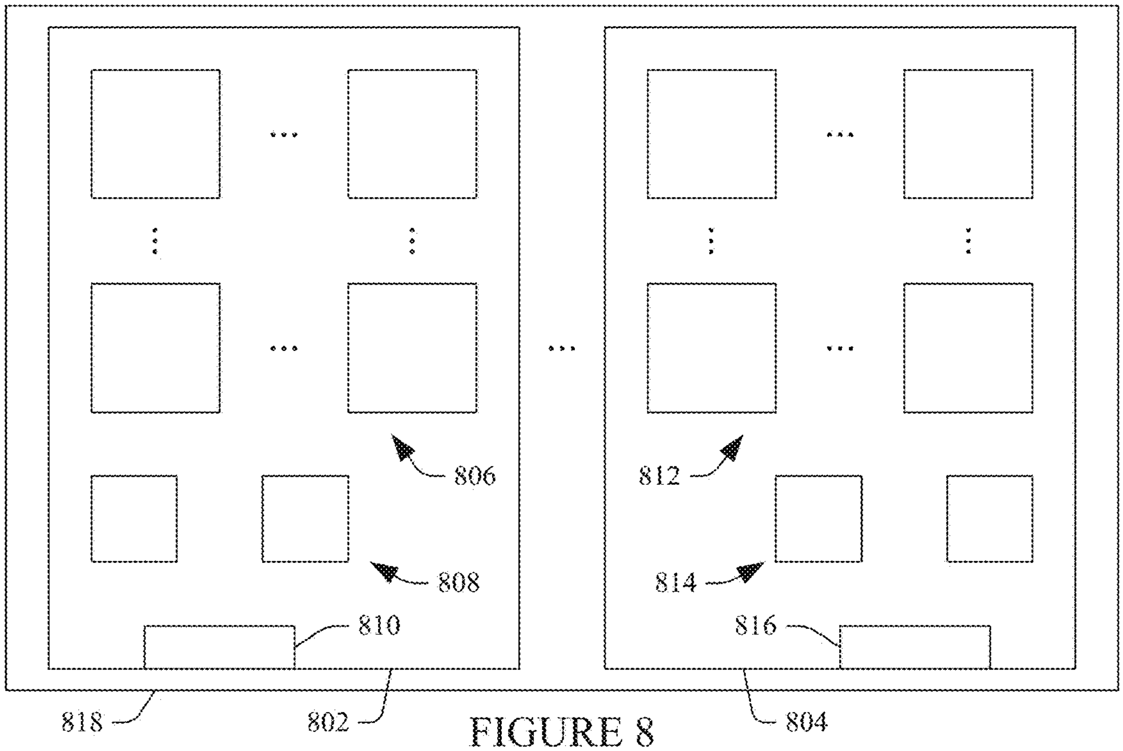
FIG. 8 schematically illustrates yet another non-limiting example of the gantry motion sensing system, in accordance with an embodiment(s) herein.

FIG. 8 schematically illustrates another variation of the gantry motion sensing system 128 (FIG. 1). In this example, the gantry motion sensing system 128 includes a circuit board 802 for one axis/plane of motion (e.g., the X direction or the Z direction) and a circuit board 804 for another axis/plane of motion (e.g., the other of the X direction or the Z direction). The circuit board 802 includes a set of motion sensors 806, motion signal processing circuitry 808 (e.g., averaging and integration circuits, etc.) and readout electronics 810. The circuit board 804 includes a set of motion sensors 812, motion signal processing circuitry 814 (e.g., averaging and integration circuits, etc.), and readout electronics 816.

Functionality of the set of motion sensors 806, the motion signal processing circuitry 808, the readout electronics 810, the set of motion sensors 812, the motion signal processing circuitry 814, and the readout electronics 816 is substantially similar to that described in connection with the set of motion sensors 602, the set of averaging circuits 604, and the readout electronics 608 of FIG. 6, with the exception that a single axis sensor or a single axis of a multi-axis sensor can be utilized on each of the circuit boards 802 and 804 since each of the circuit boards 802 and 804 is configured for a single axis/plane. The circuit board 802, . . . , and the circuit board 804 are installed on a common substrate 818.

Figure 9:
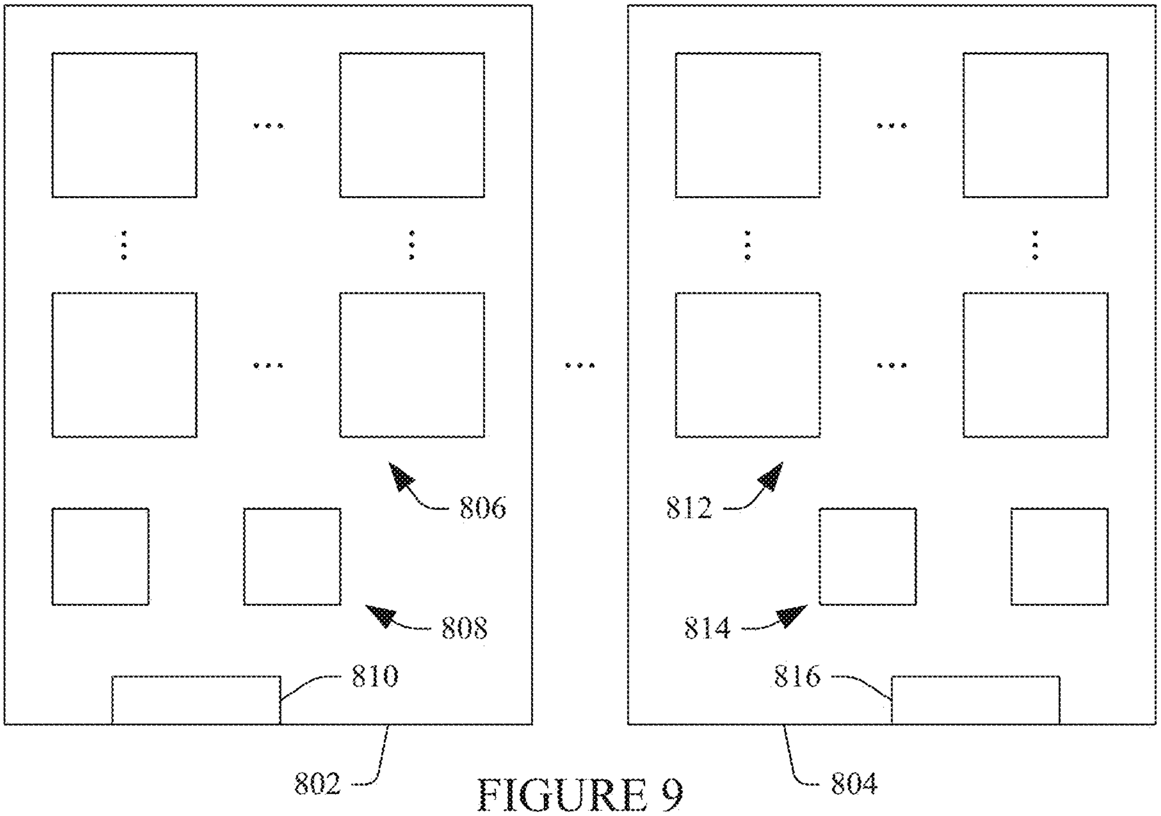
FIG. 9 schematically illustrates still another non-limiting example of the gantry motion sensing system, in accordance with an embodiment(s) herein.

FIG. 9 schematically illustrates another variation of the gantry motion sensing system 128 (FIG. 1). In this example, the gantry motion sensing system 128 is substantially similar to the variation described in connection with FIG. 9, except that the common substrate 818 is omitted, and the circuit board 802, . . . , and the circuit board 804 are each individually installed in the gantry 104.

Figure 10:
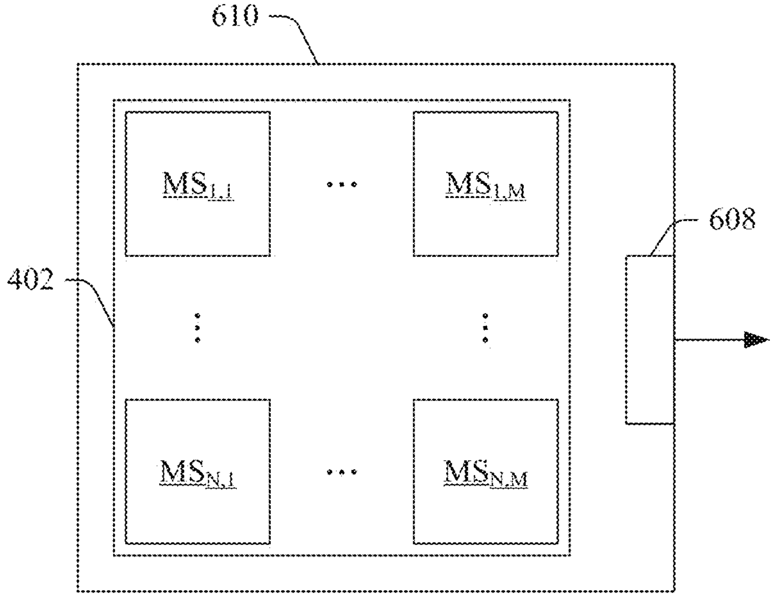
FIG. 10 schematically illustrates another non-limiting example of the gantry motion sensing system, in accordance with an embodiment(s) herein.

FIG. 10 schematically illustrates another variation of the gantry motion sensing system 128 (FIG. 1). In this example, the gantry motion sensing system 128 is substantially similar to the variation described in connection with FIG. 6, except that the motion signal processing circuitry 404 is omitted. As discussed herein, in one instance each of the motion sensors in the N×M array of motion sensors 602 is a multi-axis motion sensor, where at least one axis is assigned to sense gantry motion in one axis/plane, another axis is assigned to sense gantry motion in another axis/plane, etc., and the motion sensors in the N×M array of motion sensors 602 output acceleration values corresponding to detected gantry motion. In this example, the readout electronics 608 readout the acceleration signals. Further processing, such as integrating the acceleration signals to determine displacement values corresponding to gantry motion is performed off of the substrate 610.

Figure 11:
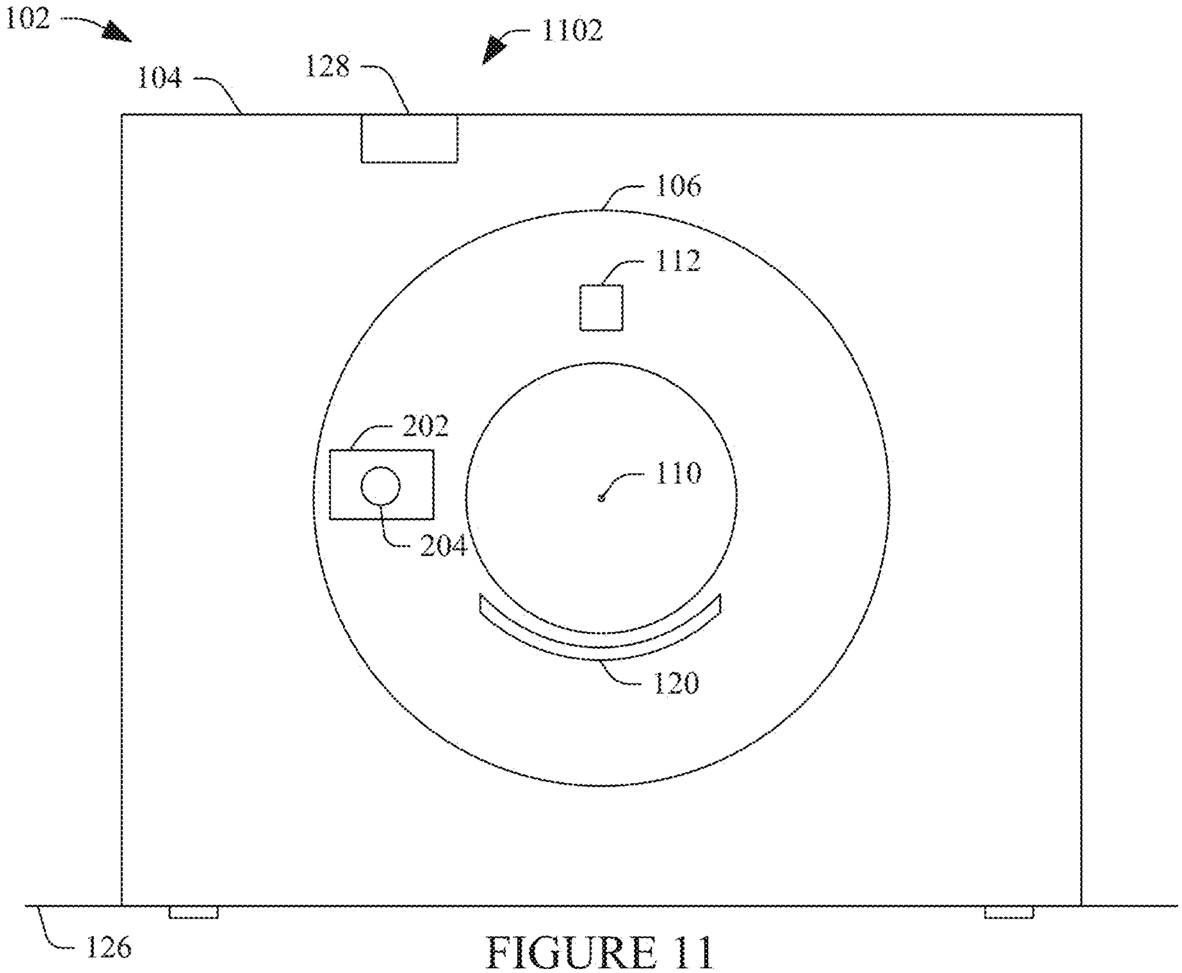
FIG. 11 schematically illustrates a non-limiting example of an inside of the gantry of the imaging system and the gantry motion sensing system installed therein, in accordance with an embodiment(s) herein.

FIG. 11 schematically illustrates an example location of the gantry motion sensing system 128 (FIG. 1) within the gantry 104. In general, with the imaging system 102 mounted to the floor 126 (FIG. 3), a higher location in the gantry 104, relative to support 126, will experience a greater degree of motion relative to a lower location in the gantry 104, since the gantry/floor interface is a pivot point. FIG. 11 shows an inside of the imaging system 102, e.g., the imaging system 102 with a front cover open or removed. In FIG. 11, the gantry motion sensing system 128 is installed in the gantry 104 near a top 1102 of the gantry 104. In addition, the gantry motion sensing system 128 is installed in the gantry 104 nearer to the rotating frame 106, facilitating coupling X and/or Z motion of the rotating frame 106 to the gantry motion sensing system 128.

Figure 12:
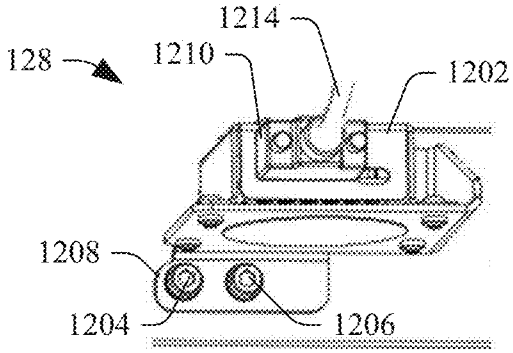
FIG. 12 schematically illustrates a magnified view of the installed gantry motion sensing system of FIG. 11, in accordance with an embodiment(s) herein.

FIG. 12 shows a magnified view of the gantry motion sensing system 128 shown in FIG. 11. In this example, the gantry motion sensing system 128 is housed in a container 1202, which is mounted in the gantry 104 via fasteners 1204 and 1206, such as screws, nuts and bolts, rivets, etc., through a mounting plate 1208 of the container 1202. An electro-mechanical connector 1214, which is complementary to the electro-mechanical connector of the readout electronics 608, is connected to the electro-mechanical connector of the readout electronics 608. The electro-mechanical connector 1210 includes a cable 1214 for routing the motion signals off the gantry motion sensing system 128. In one instance, the cable 1214 is at least part of a communications path to the operator console 138 (FIG. 1) and routes the motion signals for processing, e.g., by the gantry motion evaluation module 152 and/or otherwise.

As discussed herein, the motion signal can be utilized to balance the masses carried by the rotating gantry 106 and/or rebalance masses carried by the rotating gantry 106. An example approach is described in U.S. Pat. No. 6,890,100 B2 to Reznicek et al., entitled "CT Gantry Balance System," and filed on May 10, 2005, the entirety of which is incorporated herein by reference. With this approach, signals from multiple sensors are routed to a balance sensor buffer board, then to a subordinate board that includes filters, then to an analog-to-digital converter, and then to a microprocessor having firmware to make the certain calculations, where the output of the microprocessor is sent to a monitor and/or printer to provide balancing calculations and instructions, based on the algorithm disclosed therein.

Another example approach for balancing the masses carried by the rotating gantry 106 and/or rebalance masses carried by the rotating gantry 106 is described in U.S. Pat. No. 6,748,806 B2 to Halsmer, entitled "Dynamic balancing system for computed tomography gantry," and filed on Aug. 28, 2003, the entirety of which is incorporated herein by reference. With this approach, signals from multiple sensors are utilized to move weights to balance the gantry. In one instance, the movement of the weights may be done manually by direct control of the signals on leads through a control panel or the like. In another instance, an automatic balancing procedure is used in which balance controller utilizes the signals from the sensor and motor to provide control of the weights within the motorized weight units. Other approaches are contemplated herein.

As discussed herein, the motion signal can additionally, or alternatively, be utilized to identify and facilitate correcting insufficient or inadequate mounting of the gantry 104 to a support 126 such as an examination room floor, identify other imbalance over time, etc. In one instance, this is achieved through the gantry motion evaluation module 152 (FIG. 1) of the operator console 138 (FIG. 1). For example, at a given time period (e.g., scheduled, predetermined, on demand, etc.), the gantry motion evaluation module 152 can evaluate the signals from the gantry motion sensing system 128. For instance, the gantry motion evaluation module 152 may compare the sensed motion with a predetermined range of acceptable motion. In this instance, where the motion falls outside of the predetermined range, the gantry motion evaluation module 152 can notify personnel. In one instance, the notification may indicate a possible region of the CT imaging system 102 adding to the motion. This may include utilizing a look-up table, database, data structure, etc. that maps values of motion to possible regions.

Figure 13:
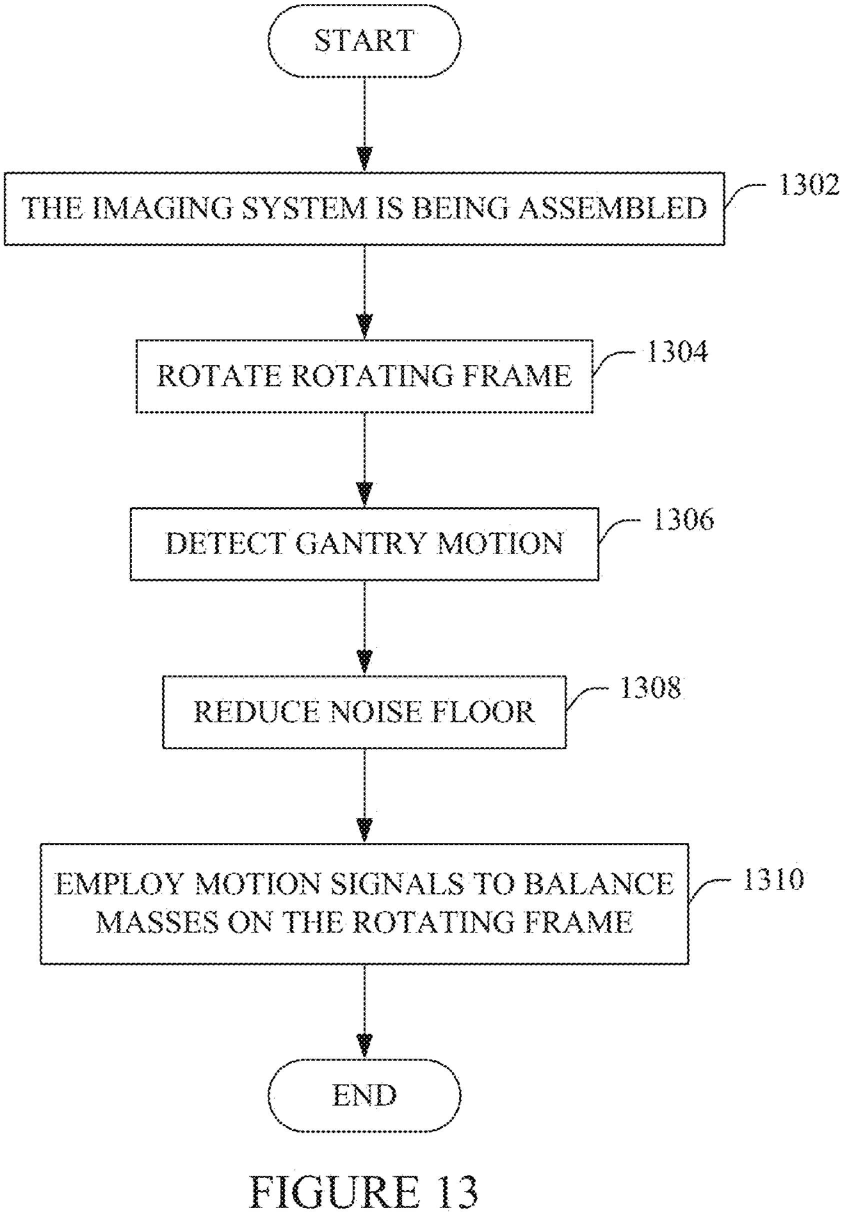
FIG. 13 illustrates a non-limiting example of a flow chart for a computer-implemented method for balancing masses carried by the rotating frame, in accordance with an embodiment(s) herein.

FIG. 13 illustrates a non-limiting example of a flow chart for a computer-implemented method for balancing masses carried by the rotating frame 106, in accordance with an aspect herein. It is to be appreciated that the ordering of the acts in the method is not limiting. As such, other orderings are contemplated herein. In addition, one or more acts may be omitted, and/or one or more additional acts may be included.

At 1302, the imaging system 102 is being assembled. In one instance, this includes installing the rotating frame 106 in the gantry 104, the X-ray source assembly 112 on the rotating frame 106, the X-ray radiation sensitive detector array 120 on the rotating frame 106, the at least one balance weight support 202 on the rotating frame 106, the gantry motion sensing system 128, etc., as described herein and/or otherwise. At 1304, the imaging system 102 is operated to rotate the rotating frame 106. At 1306, motion sensors the gantry motion sensing system 128 detect a same motion of the gantry 104, as described herein and/or otherwise.

At 1308, the gantry motion sensing system 128 processes the detected motion to reduce a noise floor of the motion sensors, as described herein and/or otherwise. At 1310, the processed motion signals are further processed and utilized to adjust the one or more balance weights 204 on the at least one balance weight support 202 to balance the masses supported by the rotating frame 106, as described herein and/or otherwise. For example, the processed motion signals can be utilized as described in U.S. Pat. No. 6,890,100 B2 and/or U.S. Pat. No. 6,748,806 B2, and/or otherwise utilized to balance the masses supported by the rotating frame 106.

Figure 14:
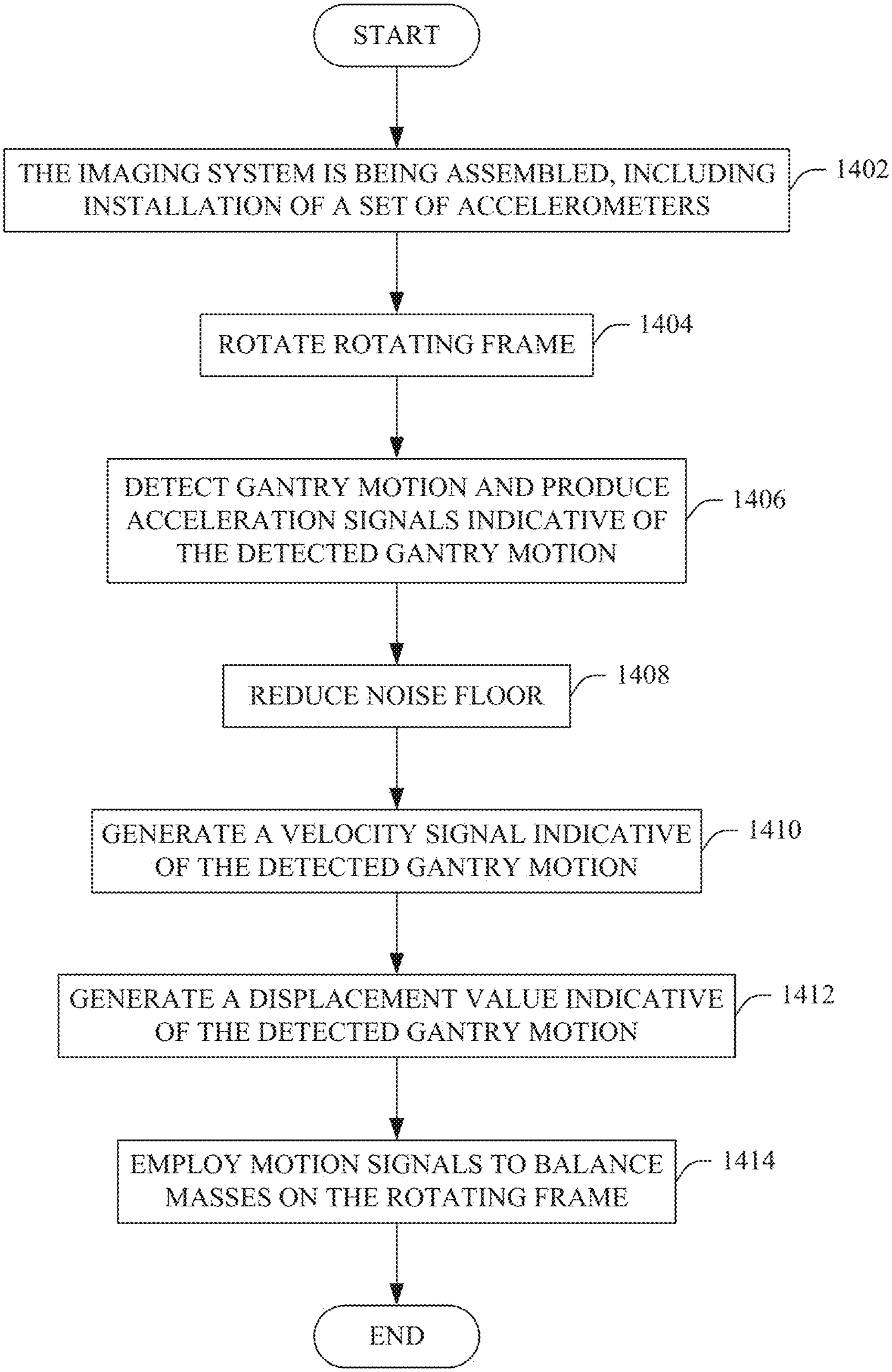
FIG. 14 illustrates another non-limiting example of a flow chart for a computer-implemented method for balancing masses carried by the rotating frame, in accordance with an embodiment(s) herein.

FIG. 14 illustrates another non-limiting example of a flow chart for a computer-implemented method for balancing masses carried by the rotating frame 104, in accordance with an aspect herein. It is to be appreciated that the ordering of the acts in the method is not limiting. As such, other orderings are contemplated herein. In addition, one or more acts may be omitted, and/or one or more additional acts may be included.

At 1402, the imaging system 102 is being assembled. In one instance, this includes installing the rotating frame 106 in the gantry 104, the X-ray source assembly 112 on the rotating frame 106, the X-ray radiation sensitive detector array 120 on the rotating frame 106, the at least one balance weight support 202 on the rotating frame 106, accelerometers of the gantry motion sensing system 128, etc., as described herein and/or otherwise. At 1404, the imaging system 102 is operated to rotate the rotating frame 106. At 1406, the accelerometers detect a same motion of the gantry 104 and output acceleration signals indicative of the detected gantry motion.

At 1408, the gantry motion sensing system 128 processes the acceleration signals to reduce a noise floor of set of the acceleration signals producing a combined acceleration signal, as described herein and/or otherwise. At 1410, the gantry motion sensing system 128 integrates the combined acceleration signal producing a velocity signal indicative of the gantry motion, as described herein and/or otherwise. At 1412, the operator console 138 processes the velocity signal producing a displacement value indicative of the gantry motion, as described herein and/or otherwise. At 1412, the displacement value is utilized to adjust the one or more balance weights 204 on the at least one balance weight support 202 to balance the masses supported by the rotating frame 106.

Figure 15:
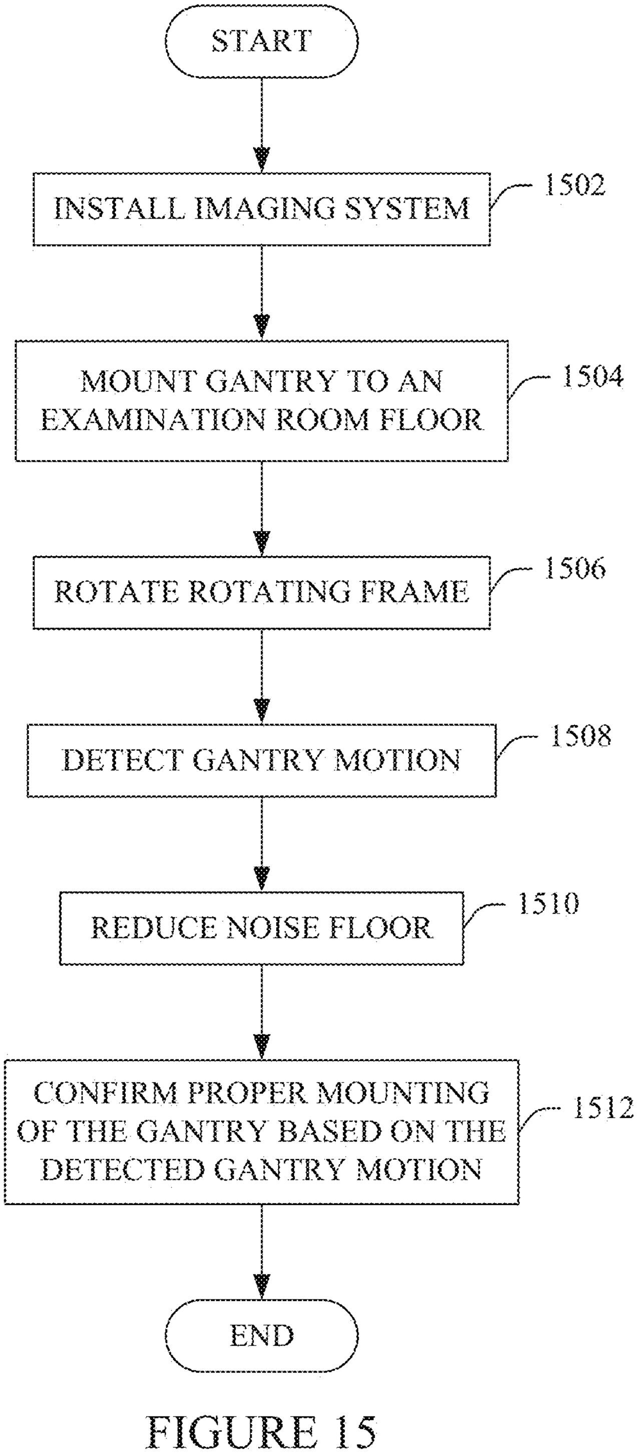
FIG. 15 illustrates a non-limiting example of a flow chart for a computer-implemented method for installing the gantry on the support, in accordance with an embodiment(s) herein.

FIG. 15 illustrates a non-limiting example of a flow chart for a computer-implemented method for installing the gantry 104 on the support 126, in accordance with an aspect herein. It is to be appreciated that the ordering of the acts in the method is not limiting. As such, other orderings are contemplated herein. In addition, one or more acts may be omitted, and/or one or more additional acts may be included.

At 1502, the imaging system 102 is being installed. At 1504, the gantry 104 is mounted to the support 126 such as an examination room floor, as described herein and/or otherwise. At 1506, the imaging system 102 is operated to rotate the rotating frame 106. At 1508, motion sensors of the gantry motion sensing system 128 detect a same motion of the gantry 104, as described herein and/or otherwise.

At 1510, the gantry motion sensing system 128 processes the detected motion to reduce a noise floor of the motion sensors producing a combined motion signal, as described herein and/or otherwise. At 1512, the combined motion signal is utilized to confirm proper mounting of the gantry 104 on the examination room floor. If needed, e.g., the confirmation is unsuccessful, the gantry 104 is reinstalled to the examination room floor 126.

Figure 16:
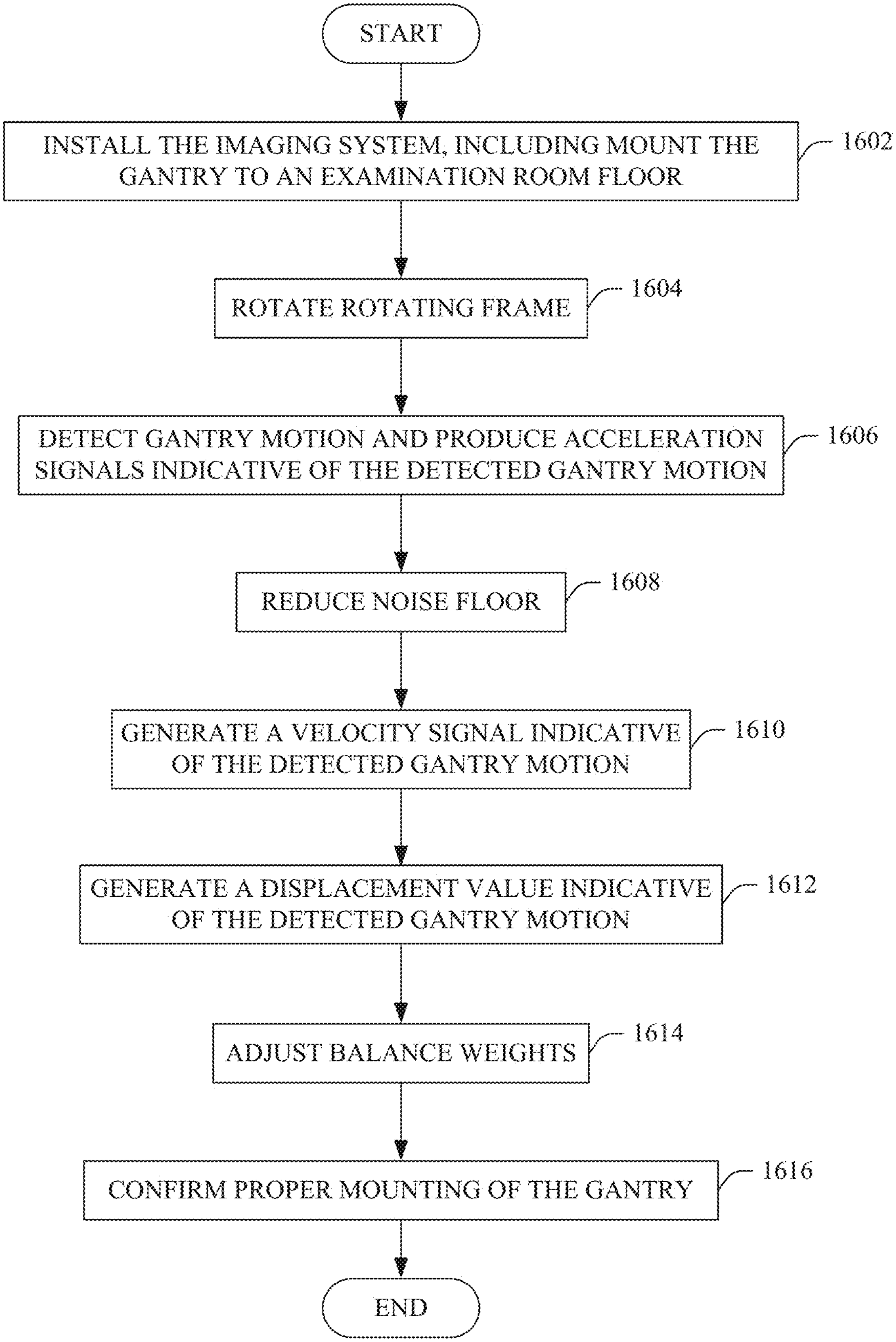
FIG. 16 illustrates a non-limiting example of a flow chart for a computer-implemented method for installing the gantry on the support, in accordance with an embodiment(s) herein.

FIG. 16 illustrates another non-limiting example of a flow chart for a computer-implemented method for installing the gantry 104 on the support 126, in accordance with an aspect of herein. It is to be appreciated that the ordering of the acts in the method is not limiting. As such, other orderings are contemplated herein. In addition, one or more acts may be omitted, and/or one or more additional acts may be included.

At 1602, the imaging system 102 is being assembled. In one instance, this includes mounting the gantry 104 on the support 126 such as an examination room floor, as described herein and/or otherwise. At 1604, the imaging system 102 is operated to rotate the rotating frame 106. At 1606, accelerometers of the gantry motion sensing system 128 detect a same motion of the gantry 104 and output acceleration signals indicative of the detected gantry motion, as described herein and/or otherwise. At 1608, the gantry motion sensing system 128 processes the acceleration signals to reduce a noise floor of the acceleration signals producing a combined acceleration signal, as described herein and/or otherwise.

At 1610, the gantry motion sensing system 128 integrates the combined acceleration signal producing a velocity signal indicative of the gantry motion, as described herein and/or otherwise. At 1612, the operator console 138 processes the velocity signal producing a displacement value indicative of the gantry motion, as described herein and/or otherwise. At 1614, the displacement value is utilized to adjust the one or more balance weights 204 on the at least one balance weight support 202 to balance the masses supported by the rotating frame 106. At 1616, the displacement values are utilized to confirm the gantry 104 is suitably installed on the support 126. If needed, e.g., the confirmation is unsuccessful, the gantry 104 is reinstalled to the examination room floor 126.

Figure 17:
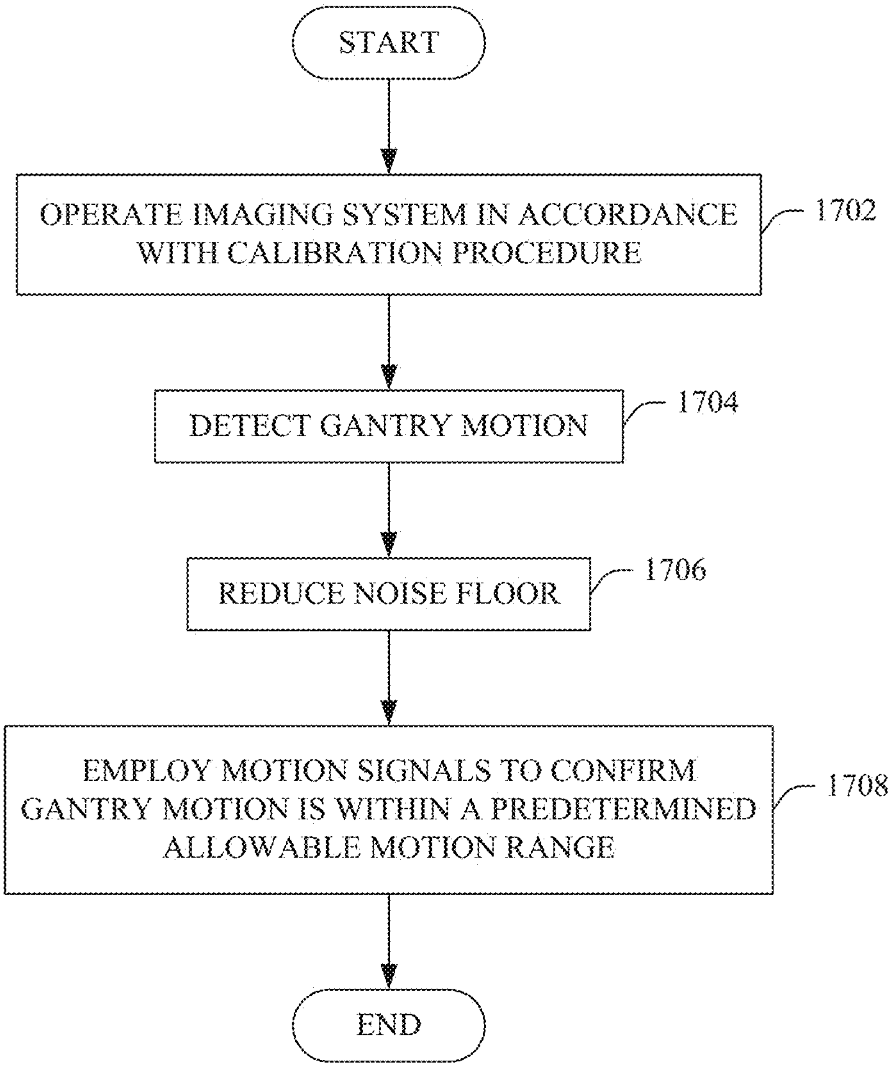
FIG. 17 illustrates a non-limiting example of a flow chart for a computer-implemented method for confirming gantry motion is within a predetermined allowable gantry motion range via a calibration procedure, in accordance with an embodiment(s) herein.

FIG. 17 illustrates a non-limiting example of a flow chart for a computer-implemented method for confirming gantry motion is within a predetermined allowable gantry motion range via a calibration procedure, in accordance with an aspect herein. It is to be appreciated that the ordering of the acts in the method is not limiting. As such, other orderings are contemplated herein. In addition, one or more acts may be omitted, and/or one or more additional acts may be included.

At 1702, the imaging system 102 is operated in accordance with a calibration procedure. At 1704, motion sensors the gantry motion sensing system 128 detect a same motion of the gantry 104, as described herein and/or otherwise. At 1706, the gantry motion sensing system 128 processes the detected motion to reduce a noise floor of the motion sensors producing a combined motion signal, as described herein and/or otherwise. At 1708, the combined motion signal is utilized to confirm gantry motion is within a predetermined allowable gantry motion range, as described herein and/or otherwise.

Figure 18:
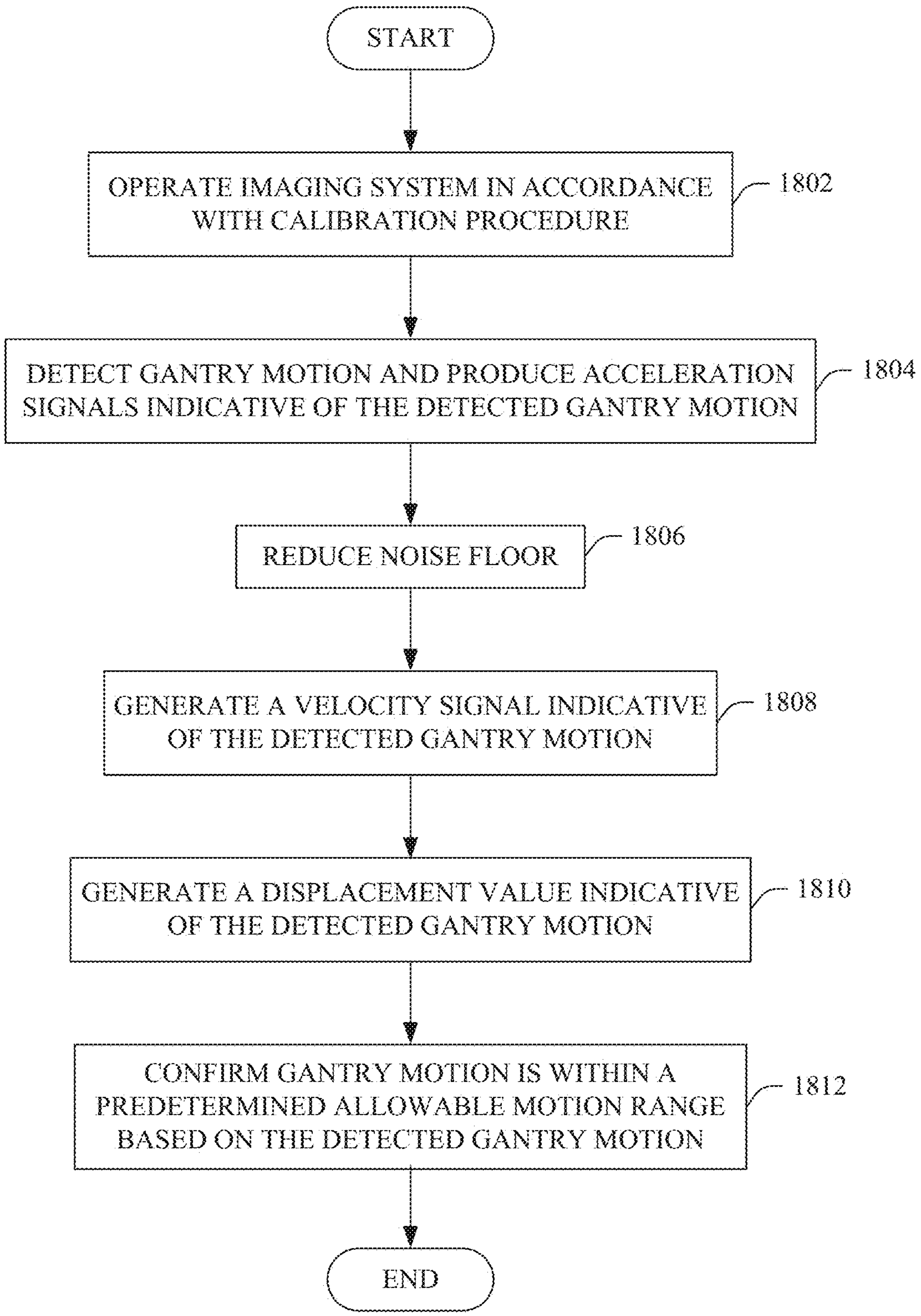
FIG. 18 illustrates another non-limiting example of a flow chart for a computer-implemented method for confirming gantry motion is within a predetermined allowable gantry motion range via a calibration procedure, in accordance with an embodiment(s) herein.

FIG. 18 illustrates another non-limiting example of a flow chart for a computer-implemented method for confirming gantry motion is within a predetermined allowable gantry motion range via a calibration procedure, in accordance with an aspect of herein. It is to be appreciated that the ordering of the acts in the method is not limiting. As such, other orderings are contemplated herein. In addition, one or more acts may be omitted, and/or one or more additional acts may be included.

At 1802, the imaging system 102 is operated in accordance with a calibration procedure. At 1804, accelerometers of the gantry motion sensing system 128 detect a same motion of the gantry 104 and output acceleration signals indicative of the detected gantry motion, as described herein and/or otherwise. At 1806, the gantry motion sensing system 128 processes the acceleration signals to reduce a noise floor of the acceleration signals producing a combined acceleration signal, as described herein and/or otherwise.

At 1808, the gantry motion sensing system 128 integrates the combined acceleration signal producing a velocity signal indicative of the gantry motion, as described herein and/or otherwise. At 1810, the operator console 138 processes the velocity signal producing a displacement value indicative of the gantry motion, as described herein and/or otherwise. At 1812, the displacement value is utilized to confirm gantry motion is within a predetermined allowable gantry motion range, as described herein and/or otherwise.

The above can be implemented by way of computer readable instructions, encoded, or embedded on the computer readable storage medium, which, when executed by a computer processor, cause the processor to carry out the described acts or functions. Additionally, or alternatively, at least one of the computer readable instructions is carried out by a signal, carrier wave or other transitory medium, which is not computer readable storage medium.

As used herein, an element or step recited in the singular and proceeded with the word “a” or “an” should be understood as not excluding plural of said elements or steps, unless such exclusion is explicitly stated. Furthermore, references to “one embodiment” of the present invention are not intended to be interpreted as excluding the existence of additional embodiments that also incorporate the recited features. Moreover, unless explicitly stated to the contrary, embodiments “comprising,” “including,” or “having” an element or a plurality of elements having a particular property may include such additional elements not having that property. The terms “including” and “in which” are used as the plain-language equivalents of the respective terms “comprising” and “wherein.” Moreover, the terms “first,” “second,” and “third,” etc. are used merely as labels, and are not intended to impose numerical requirements or a particular positional order on their objects.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term “computer” or “module” may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present disclosure. That is, features of the described embodiments can be combined with any appropriate aspect described above and optional features of any one aspect can be combined with any other appropriate aspects. Similarly, features set forth in dependent claims can be combined with non-mutually exclusive features of other dependent claims, particularly where the dependent claims depend on the same independent claim. Single claim dependencies may have been used as practice in some jurisdictions that require them, but this should not be taken to mean that the features in the dependent claims are mutually exclusive.

What is claimed is:

1. A computed tomography imaging system, comprising:

a gantry;

a rotating frame rotatably supported in the gantry and carrying at least one component for producing, transmitting or receiving X-ray radiation;

a first motion sensor configured to sense a first motion of the gantry in a first plane and generate a first signal indicative of the first motion, wherein the first signal has a first noise floor;

a second motion sensor configured to concurrently sense the first motion of the gantry in the first plane and generate a second signal indicative of the first motion, wherein the second signal has a second noise floor; and motion signal processing circuitry configured to combine the first signal and the second signal to generate a first combined signal indicative of the first motion, wherein the first combined signal has a third noise floor that is lower than the first noise floor and the second noise floor.

2. The computed tomography imaging system of claim 1, wherein the motion signal processing circuitry employs a root-sum-square algorithm to average a combination of the first signal and the second signal to generate the first combined signal.

3. The computed tomography imaging system of claim 1, wherein the first combined signal is a first acceleration signal, and the motion signal processing circuitry is further configured to process the first acceleration signal and generate a first velocity signal, and further comprising:

readout electronics configured to readout the first velocity signal.

4. The computed tomography imaging system of claim 3, further comprising:

a processor configured to execute computer instructions in a memory which cause the processor to process the first velocity signal to determine a displacement value corresponding to the gantry motion.

5. The computed tomography imaging system of claim 4, wherein the rotating frame further includes a balance weight support configured to support one or more balance weights that balance a total mass carried by the rotating gantry based on the displacement value.

6. The computed tomography imaging system of claim 4, wherein the gantry includes a mounting bracket configured to mount to an examination room floor in accordance with an installation procedure based on the displacement value.

7. The computed tomography imaging system of claim 1, wherein the first motion sensor is further configured to sense a second first motion of the gantry in a second plane and generate a third signal indicative of the second motion, wherein the third signal has a fourth noise floor; and wherein the second motion sensor is further configured to sense the second motion of the gantry in the second plane and generate a fourth signal indicative of the second motion, wherein the fourth signal has a fifth noise floor; and wherein the motion signal processing circuitry is further configured to combine the third signal and the fourth signal to generate a second combined signal, wherein the second combined signal has a sixth noise floor that is lower than the fourth noise floor and the fifth noise floor.

8. The computed tomography imaging system of claim 1, wherein the first motion sensor and the second motion sensor are affixed in the gantry.

9. The computed tomography imaging system of claim 1, further comprising:

a circuit board configured to carry the first motion sensor, the second motion sensor, and the motion signal processing circuitry.

10. The computed tomography imaging system of claim 1, wherein the first motion sensor includes a first accelerometer and the second motion sensor includes a second accelerometer.

11. A computer-implemented method, comprising:

detecting a first motion of a gantry of a computed tomography imaging system in a first plane with a first motion sensor;

generating a first signal indicative of the first motion, wherein the first signal has a first noise floor;

detecting, concurrently with detecting the first motion with the first motion sensor, the first motion of the gantry with a second motion sensor;

generating a second signal indicative of the first motion, wherein the second signal has a first noise floor; and combining the first signal and the second signal into a first combined signal, wherein the first combined signal has a third noise floor that is lower than the first noise floor and the second noise floor;

wherein the first combined signal is used to determine a first displacement value corresponding to the first plane of the gantry motion.

12. The computer-implemented method of claim 11, further comprising:

detecting a second motion of the gantry in a second plane with the first motion sensor;

generating a third signal indicative of the second motion, wherein the third signal has a fourth noise floor;

detecting, concurrently with detecting the second motion with the first motion sensor, the second motion of the gantry with a second motion sensor;

generating a fourth signal indicative of the second motion, wherein the fourth signal has a fifth noise floor; and combining the third signal and the fourth signals into a second combined signal, wherein the second combined signal has a sixth noise floor that is lower than the fourth noise floor and the fifth noise floor.

13. The computer-implemented method of claim 12, wherein combining the first signal and the second signal includes averaging a combination of the first signal and the second signal using a root-sum-square algorithm, and combining the third signal and the fourth signal includes averaging a combination of the third signal and the fourth signal using a root-sum-square algorithm.

14. The computer-implemented method of claim 13, wherein the first combined signal is a first acceleration signal and the second combined signal is a second acceleration signal, and further comprising:

integrating the first acceleration signal to generate a first velocity signal;

integrating the second acceleration signal to generate a second velocity signal; and reading out the first velocity signal and the second velocity signal.

15. The computer-implemented method of claim 14, further including: integrating the first velocity signal to determine the first displacement value corresponding to the first plane of the gantry motion; and integrating the second velocity signal to determine a second displacement value corresponding to the second plane of the gantry motion.

16. A non-transitory computer readable medium encoded with computer executable instructions, which, when executed by a processor, causes the processor to:

detect a first motion of a gantry of a computed tomography imaging system in a first plane with a first motion sensor;

generate a first signal indicative of the first motion, wherein the first signal has a first noise floor;

detect, concurrently with detecting the first motion with the first motion sensor, the first motion of the gantry with a second motion sensor;

generate a second signal indicative of the first motion, wherein the second signal has a first noise floor; and combine the first signal and the second signal into a first combined signal, wherein the first combined signal has a third noise floor that is lower than the first noise floor and the second noise floor;

wherein the first combined signal is used to determine a first displacement value corresponding to the first plane of the gantry motion.

17. The non-transitory computer readable medium of claim 16, wherein the computer executable instructions further cause the processor to: detect a second motion of the gantry in a second plane with the first motion sensor; generate a third signal indicative of the second motion, wherein the third signal has a fourth noise floor; detect, concurrently with detecting the second motion with the first motion sensor, the second motion of the gantry with a second motion sensor; generate a fourth signal indicative of the second motion, wherein the fourth signal has a fifth noise floor; and combine the third signal and the fourth signals into a second combined signal, wherein the second combined signal has a sixth noise floor that is lower than the fourth noise floor and the fifth noise floor.

18. The non-transitory computer readable medium of claim 17, wherein the computer executable instructions further cause the processor to: combine the first signal and the second signal by averaging a combination of the first signal and the second signal using a root-sum-square algorithm; and combine the third signal and the fourth signal by averaging a combination of the third signal and the fourth signal using a root-sum-square algorithm.

19. The non-transitory computer readable medium of claim 18, wherein the first combined signal is a first acceleration signal and the second combined signal is a second acceleration signal, and the computer executable instructions further cause the processor to: integrate the first acceleration signal to generate a first velocity signal; integrate the second acceleration signal to generate a second velocity signal; and read out the first velocity signal and the second velocity signal.

20. The non-transitory computer readable medium of claim 19, wherein the computer executable instructions further cause the processor to: integrate the first velocity signal to determine the first displacement value corresponding to the first plane of the gantry motion; and integrate the second velocity signal to determine a second displacement value corresponding to the second plane of the gantry motion.

* * * * *